(12) United States Patent
Swerdlow

(10) Patent No.: US 10,543,364 B2
(45) Date of Patent: Jan. 28, 2020

(54) DETECTION OF LEAD ELECTRODE DISLODGEMENT USING CAVITARY ELECTROGRAM

(71) Applicant: Lambda Nu Technology LLC, Orono, MN (US)

(72) Inventor: Charles Swerdlow, Los Angeles, CA (US)

(73) Assignee: Lambda Nu Technology LLC, Orono, MN (US)

(*) Notice: Subject to any disclaimer, the term of this patent is extended or adjusted under 35 U.S.C. 154(b) by 42 days.

(21) Appl. No.: 15/678,858

(22) Filed: Aug. 16, 2017

(65) Prior Publication Data

US 2018/0289952 A1 Oct. 11, 2018

Related U.S. Application Data

(60) Provisional application No. 62/482,822, filed on Apr. 7, 2017.

(51) Int. Cl.
*A61N 1/05* (2006.01)
*A61N 1/08* (2006.01)
(Continued)

(52) U.S. Cl.
CPC ............ *A61N 1/0563* (2013.01); *A61N 1/08* (2013.01); *A61N 1/37282* (2013.01); *A61N 1/3925* (2013.01); *A61N 1/3956* (2013.01)

(58) Field of Classification Search
CPC ...... A61N 1/0563; A61N 1/3925; A61N 1/08; A61N 2001/083
See application file for complete search history.

(56) References Cited

U.S. PATENT DOCUMENTS

| 3,599,055 A | 8/1971 | Bloom |
| 4,766,549 A | 8/1988 | Schweitzer, III et al. |

(Continued)

FOREIGN PATENT DOCUMENTS

| EP | 0288630 B1 | 11/1988 |
| EP | 2032027 B1 | 10/2011 |

OTHER PUBLICATIONS

"Agilent Impedance Measurement Handbook a Guide to Measurement Technology and Techniques 4th Edition," Agilent Technologies, Inc., Jun. 17, 2009, 140 pages.

(Continued)

*Primary Examiner* — Joseph M Dietrich
(74) *Attorney, Agent, or Firm* — Patterson Thuente Pedersen, P.A.

(57) ABSTRACT

Methods and systems for identifying dislodgement of an electrode, operably coupled to an implanted medical device, from fixation with the endocardium of a chamber of the heart of a patient can include obtaining a test electrogram, and measuring at least two parameters indicating a cavitary electrogram and taking an action, such as generating an electrode dislodgement alert and/or configuring the implanted medical device to disable therapy, when the cavitary electrogram is indicated. In embodiments, the two parameters include a test positive component magnitude and a test negative component magnitude. In embodiments, the test component magnitudes are compared to baseline component magnitudes determined from a baseline electrogram.

29 Claims, 8 Drawing Sheets

(51) Int. Cl.
*A61N 1/39* (2006.01)
*A61N 1/372* (2006.01)

(56) References Cited

U.S. PATENT DOCUMENTS

| | | | |
|---|---|---|---|
| 5,003,975 A | 4/1991 | Hafelfinger et al. |
| 5,231,987 A | 8/1993 | Robson |
| 5,243,980 A | 9/1993 | Mehra |
| 5,361,776 A | 11/1994 | Samuelson et al. |
| 5,405,363 A | 4/1995 | Kroll et al. |
| 5,453,698 A | 9/1995 | Williams et al. |
| 5,545,186 A | 8/1996 | Olson et al. |
| 5,557,210 A | 9/1996 | Cappa et al. |
| 5,713,932 A | 2/1998 | Gillberg et al. |
| 5,741,311 A | 4/1998 | McVenes et al. |
| 5,755,736 A | 5/1998 | Gillberg et al. |
| 5,755,742 A | 5/1998 | Schuelke et al. |
| 5,897,577 A | 4/1999 | Cinbis et al. |
| 5,944,746 A | 8/1999 | Kroll |
| 6,104,954 A | 8/2000 | Blunsden |
| 6,259,947 B1 | 7/2001 | Olson et al. |
| 6,317,633 B1 | 11/2001 | Jorgenson et al. |
| 6,415,179 B1 | 7/2002 | Pendekanti et al. |
| 6,445,951 B1 | 9/2002 | Mouchawar |
| 6,490,486 B1 | 12/2002 | Bradley |
| 6,580,948 B2 | 6/2003 | Haupert et al. |
| 6,928,325 B2 | 8/2005 | Zhu et al. |
| 6,980,860 B2 | 12/2005 | Stadler et al. |
| 7,047,083 B2 | 5/2006 | Gunderson et al. |
| 7,081,130 B2 | 7/2006 | Jang |
| 7,120,563 B2 | 10/2006 | Bechhoefer et al. |
| 7,289,851 B2 | 10/2007 | Gunderson et al. |
| 7,333,855 B2 | 2/2008 | Gunderson et al. |
| 7,369,893 B2 | 5/2008 | Gunderson |
| 7,454,249 B1 | 11/2008 | Bornzin et al. |
| 7,623,919 B2 | 11/2009 | Goetz et al. |
| 7,747,320 B1 | 6/2010 | Kroll et al. |
| 7,764,998 B1 | 7/2010 | Raddatz |
| 8,200,330 B2 | 6/2012 | Kroll et al. |
| 8,209,007 B2 | 6/2012 | McIntyre et al. |
| 8,352,033 B2 | 1/2013 | Kroll |
| 8,457,742 B2 | 6/2013 | Jacobson |
| 8,463,382 B2 | 6/2013 | Jorgenson et al. |
| 8,463,384 B2 | 6/2013 | Germanson et al. |
| 8,467,872 B2 | 6/2013 | Hareland |
| 8,498,706 B2 | 7/2013 | Pei et al. |
| 8,577,457 B2 | 11/2013 | Miller et al. |
| 8,644,932 B2 | 2/2014 | Seifert et al. |
| 8,682,436 B2 | 3/2014 | Ghosh et al. |
| 8,700,156 B2 | 4/2014 | Kroll |
| 8,781,585 B2 | 7/2014 | Gunderson et al. |
| 8,812,103 B2 | 8/2014 | Kroll et al. |
| 8,825,158 B2 | 9/2014 | Swerdlow |
| 9,272,150 B2 | 3/2016 | Kroll et al. |
| 9,427,577 B2 | 8/2016 | Kroll et al. |
| 9,486,624 B2 | 11/2016 | Swerdlow |
| 9,675,799 B2 | 6/2017 | Kroll et al. |
| 9,814,876 B2 | 11/2017 | Swerdlow |
| 9,821,156 B2 | 11/2017 | Kroll et al. |
| 9,827,416 B2 | 11/2017 | Swerdlow |
| 9,987,485 B2 | 6/2018 | Kroll et al. |
| 10,039,919 B2 | 8/2018 | Kroll et al. |
| 10,118,031 B2 | 11/2018 | Kroll et al. |
| 10,195,420 B2 | 2/2019 | Swerdlow |
| 2003/0004552 A1 | 1/2003 | Plombon et al. |
| 2003/0036772 A1 | 2/2003 | Saphon et al. |
| 2004/0010303 A1 | 1/2004 | Bolea et al. |
| 2004/0068301 A1 | 4/2004 | Waltman et al. |
| 2004/0158290 A1 | 8/2004 | Girouard et al. |
| 2004/0230385 A1 | 11/2004 | Bechhoefer et al. |
| 2005/0137636 A1 | 6/2005 | Gunderson et al. |
| 2005/0187586 A1 | 8/2005 | David et al. |
| 2005/0256547 A1 | 11/2005 | Stahmann et al. |
| 2006/0025828 A1 | 2/2006 | Armstrong et al. |
| 2006/0116747 A1 | 6/2006 | Eick et al. |
| 2006/0135886 A1 | 6/2006 | Lippert et al. |
| 2006/0241513 A1 | 10/2006 | Hatlestad |
| 2006/0265038 A1 | 11/2006 | Hagen et al. |
| 2007/0208387 A1 | 9/2007 | Mower |
| 2008/0208271 A1 | 8/2008 | Sih et al. |
| 2008/0309351 A1 | 12/2008 | Stewart et al. |
| 2009/0099615 A1 | 4/2009 | Kroll |
| 2009/0270938 A1 | 10/2009 | Pei et al. |
| 2009/0292331 A1 | 11/2009 | Gunderson et al. |
| 2009/0299431 A1 | 12/2009 | Schecter |
| 2009/0299432 A1 | 12/2009 | Stadler et al. |
| 2009/0306735 A1 | 12/2009 | Lagercrantz et al. |
| 2010/0179446 A1 | 7/2010 | Bojovic et al. |
| 2010/0179538 A1 | 7/2010 | Podhajsky |
| 2010/0204758 A1 | 8/2010 | Boon et al. |
| 2010/0228307 A1 | 9/2010 | Kroll et al. |
| 2010/0324629 A1 | 12/2010 | Jorgenson et al. |
| 2011/0054554 A1 | 3/2011 | Swerdlow |
| 2011/0054556 A1 | 3/2011 | Swerdlow |
| 2011/0054558 A1* | 3/2011 | Gunderson ............ A61N 1/08 607/27 |
| 2011/0160808 A1 | 6/2011 | Lyden et al. |
| 2011/0160829 A1 | 6/2011 | Foster et al. |
| 2011/0230741 A1 | 9/2011 | Liang et al. |
| 2012/0035491 A1 | 2/2012 | Mahajan et al. |
| 2012/0191153 A1 | 7/2012 | Swerdlow et al. |
| 2012/0197331 A1 | 8/2012 | Germanson et al. |
| 2012/0197365 A1 | 8/2012 | Germanson et al. |
| 2013/0013038 A1 | 1/2013 | Miller |
| 2013/0030496 A1 | 1/2013 | Karamanoglu et al. |
| 2013/0123871 A1 | 5/2013 | Kroll |
| 2013/0165986 A1 | 6/2013 | Ghosh et al. |
| 2013/0304139 A1 | 11/2013 | Musley et al. |
| 2013/0304160 A1 | 11/2013 | Gunderson et al. |
| 2013/0325079 A1 | 12/2013 | Kroll et al. |
| 2013/0325080 A1 | 12/2013 | Kroll et al. |
| 2014/0018873 A1 | 1/2014 | Gunderson |
| 2014/0155947 A1 | 6/2014 | Kroll et al. |
| 2014/0324123 A1 | 10/2014 | Kroll et al. |
| 2014/0371831 A1 | 12/2014 | Swerdlow |
| 2015/0005862 A1 | 1/2015 | Kroll et al. |
| 2015/0088213 A1 | 3/2015 | Swerdlow |
| 2015/0151118 A1 | 6/2015 | Kroll et al. |
| 2015/0273225 A1 | 10/2015 | Swerdlow et al. |
| 2016/0250462 A1 | 9/2016 | Kroll et al. |
| 2016/0271390 A1 | 9/2016 | Kroll et al. |
| 2016/0375239 A1 | 12/2016 | Swerdlow |
| 2017/0120045 A1 | 5/2017 | Swerdlow |
| 2018/0369578 A1 | 12/2018 | Kroll et al. |

OTHER PUBLICATIONS

Armour, Andrew J., et al., "Gross and Microscopic Anatomy of the Human Intrinsic Cardiac Nervous System," Anatomical Record, 1997, pp. 289-298.

Balkhy, Husam H., et al., "Autonomic Ganglionated Plexi: Characterization and Effect of Epicardial Microwave Ablation in a Canine Model of Vagally Induced Actue Atrial Fibrillation," Meeting for the International Society for Minimally Invasive Cardiothoracic Surgery (Abstract), 2006.

Brewer et al., "Low Voltage Shocks Have a Significantly Higher Tilt of the Internal Electric Field Than Do High Voltage Shocks," Angeion Corporation, Jan. 1995, Part II, PACE, vol. 18, pp. 214-220.

Chevalier, P., "Quantitative Study of Nerves of the Human Left Atrium," Heart Rhythm, 2005, pp. 518-522.

Dilling-Boer, Dagmara et al., "Ablation of Focally Induced Atrial Fibrillation: Selective or Extensive?," J. Cardio. Electryphys., 2004, pp. 200-205.

Haissaguerre, Michel et al., "Pulmonary Veins in the Substrate for Atrial Fibrillation: The "venous wave" Hypothesis," 2004, pp. 2290-2292.

Haissaguerre, Michel et al., "Spontaneous Initiation of Atrial Fibrillation by Ecoptic Beats Originating in the Pulmonary Veins," NEJM, 2006, pp. 659-666.

(56) References Cited

OTHER PUBLICATIONS

Kilgore, K.L., et al., "Nerve Conduction Block Utilising High-Frequency Alternating Current," Med. Biol. Eng. Comput., 2004, pp. 394-406.
Kumagai, K., et al., "Electrophysiologic Properties of Pulmonary Veins Assessed Using a Multielectrode Basket Catheter," 2004, pp. 2281-2289.
Levy, S., "Characterization of Different Subsets of Atrial Fibrillation in General Practice in France: The ALFA Study," The College of French Cardiologists, Circulation, 1999, pp. 3028-3035.
Lo et al., "Noise-Doman Reflectometry for Locating Wiring Faults," IEEE Transactions on Electromagnetic Compatibility, vol. 47, No. 1, Feb. 2005.
Nathan, H., et al., "The Junction Between the Left Atrium and the Pulmonary Veins: An Anatomic Study of Human Hearts," Circulation, 1966, pp. 412-422.
Oh., S., "Vagal Denervation and Atrial Fibrillation Inducibility: Epicardial Fat Pad Ablation Does Not Have Long-Term Effects," Heart Rhythm, 2006, pp. 701-708.
Oral, Hakan et al., "Pulmonary Vein Isolation for Paroxysmal and Persistent Atrial Fibrillation," Circulation, 2002, pp. 1077-1081.
Pappone, Carlo, "Pulmonary Vein Denervation Enhances Long-Term Benefit After Circumferential Ablation for Paroxysmal Atrial Fibrillation," Circulation, 2004, pp. 327-334.
Patterson, E. et al., "Triggered Firing in Pulmonary Veins Initiated by In Vitro autonomic nerve stimulation," Heart Rhythm, 2005, pp. 624-631.
Patterson, Eugene et al., "Sodium-Calcium Exchange Initiated by the Ca2+ Transient: An Arrhythimia Trigger Within Pulmonary Veins," J. Am. Coll. Cardiol, 2006, pp. 1196-1206.
Po Sunny S., et al., "Rapid and Stable Re-entry within the Pulmonary Vein as a Mechanism Initiating Paroxysmal Atrial Fibrillation," J.Am Coll. Cariol., 2005, pp. 1871-1877.
Po, Sunny S. et al., "Experimental Model for Paroxysmal Atrial Fibrillation Arising at the Pulmonary Vein-Atrial Junctions," Heart Rhythm, 2006, pp. 201-208.
Randall, David C., et al., "Ablation of Posterior Atrial Ganglionated Plexus Potentiates Sympathetic Tachycardia to Behavioral Stress," Comp. Physiol., 1998, pp. 779-787.
Schauerte, P., et al., "Ventricular Rate Control During Atrial Fibrillation by Cardiac Parasympathetic Nerve Stimulation: A Transvenous Approach," J. Am. Coll. Cardiol., 1999, pp. 2043-2050.
Schauerte, Patrick et al., "Catheter Ablation of Cardiac Autonomic Nerves for Prevention of Vagal Atrial Fibrillation," Circulation, 2000, pp. 2774-2780.
Schauerte, Patrick, "Focal Atrial Fibrillation: Experimental Evidence for a Pathophysiologic Role of the Autonomic Nervous System," Cardiovasc. Electrophysiol., 2001, pp. 592-599.
Scherlag, Benjamin J., et al., "Autonomically Induced Conversion of Pulmonary Vein Focal Firing Into Atrial Fibrillation," J. Am Coll. Cardiol., 2005, pp. 1878-1886.
Scherlag, Benjamin, "Electrical Stimulation to Identify Neural Elements on the Heart: Their Role in Atrial Fibrillation," J. Interv. Card, Electrophysiol, 2005, pp. 37-42.
Tai, C., "Stimulation Analysis of Conduction Block in Unmyelinated Axons Induced by High-Frequency Biphasic Electrical Currents," IEEE T-BME, 2005, p. 1323.
Tchou et al., "The AngeMed Sentinel Implantable Antitachycardia Pacer Cardioverter-Defibrillator," Implantable Cardioverter-Defibrillators: A Comprehensive Textbook, Copyright 1994, pp. 755-761.
Tomasic, "Acute and Chronic High-Frequency Properties of Cardiac Pacing and Defibrillation Leads," Med Biol Eng Comput 50:827-837, 2012.
Ellenbogen, "Performance of ICD Lead Integrity Alert to Assist in the Clinical Diagnosis of ICD Lead Failures: Analysis of Different ICD Leads," Circulation Arrhythmia and Electrophysiology, Oct. 7, 2013.
Swerdlow, "Downloadable Algorithm to Reduce Inappropriate Shocks Caused by Fractures of Implantable Cardioverter-Defibrillator Leads," Circulation Journal of the American Heart Association, Nov. 3, 2008, 9 pages.
Swerdlow, "Downloadable Software Algorithm Reduces Inappropriate Shocks Caused by Implantable Cardioverter-Defibrillator Lead Fractures—A Prospective Study," Circulation Journal of the American Heart Association, Sep. 27, 2010, 8 pages.
Iwasawa J, et al., "Discrimination algorithm of an implantable cardioverter defibrillator in a case with a lead dislodgement," Heart Rhythm, vol. 11, 2014, pp. S491-S492.
Ruiz-Salas A, et al., "Inappropriate shock due to late dislocation of electrode," International Journal of Cardiology, vol. 199, 2015, pp. 229-231.
Veltmann C, et al., "Fatal inappropriate ICD shock," J. Cardiovasc. Electrophysiol, vol. 18(3), 2007, pp. 326-328.
PCT Application No. PCT/US2013/043386, filed May 30, 2013, Search Report and Written Opinion dated Sep. 27, 2013, 10 pages.
PCT Application No. PCT/US2013/043389, filed May 30, 2013, Search Report and Written Opinion dated Sep. 5, 2013, 9 pages.
PCT Application No. PCT/US2013/072957, Filed Dec. 4, 2013, Search Report and Written Opinion dated Mar. 6, 2014.
PCT Application No. PCT/US2015/022435, Filed Mar. 25, 2015, Search Report and Written Opinion dated Jun. 29, 2015.
EP Application No. 13796833.5, Extended EP Search Report dated Feb. 11, 2016, 9 pages.
European Extended Search Report; EP Application No. 13859688.7, dated May 27, 2016, 11 pages.
Application and File history for U.S. Appl. No. 12/868,056, filed Aug. 25, 2010, now U.S. Pat. No. 8,825,158.
Application and File history for U.S. Appl. No. 13/735,599, filed Jan. 7, 2013, now U.S. Pat. No. 8,700,156.
Application and File history for U.S. Appl. No. 13/842,838, filed Mar. 15, 2013.
Application and File history for U.S. Appl. No. 12/252,310, filed Oct. 15, 2008, now U.S. Pat. No. 8,352,033.
Application and File history for U.S. Appl. No. 13/843,145, filed Mar. 15, 2013, now U.S. Pat. No. 8,812,103.
Application and File history for U.S. Appl. No. 13/833,477, filed Mar. 15, 2013.
Application and File history for U.S. Appl. No. 14/224,876, filed Mar. 25, 2014.
Application and File history for U.S. Appl. No. 14/224,281, filed Mar. 25, 2014.
Application and File history for U.S. Appl. No. 14/203,688, filed Mar. 11, 2014.
Application and File history for U.S. Appl. No. 14/224,335, filed Mar. 25, 2014.
Application and File history for U.S. Appl. No. 14/453,679, filed Aug. 7, 2014.
Application and File history for U.S. Appl. No. 14/472,027, filed Aug. 28, 2014.
Application and File history for U.S. Appl. No. 15/054,538, filed Feb. 26, 2016.
Application and File history for U.S. Appl. No. 15/080,343, filed Mar. 24, 2016.
Application and File history for U.S. Appl. No. 15/344,864, filed Nov. 7, 2016.
Application and File history for U.S. Appl. No. 15/013,201, filed Feb. 4, 2016.
Application and File history for U.S. Appl. No. 15/810,324, filed Nov. 13, 2017.
Application and File history for U.S. Appl. No. 15/356,962, filed Nov. 21, 2016.

\* cited by examiner

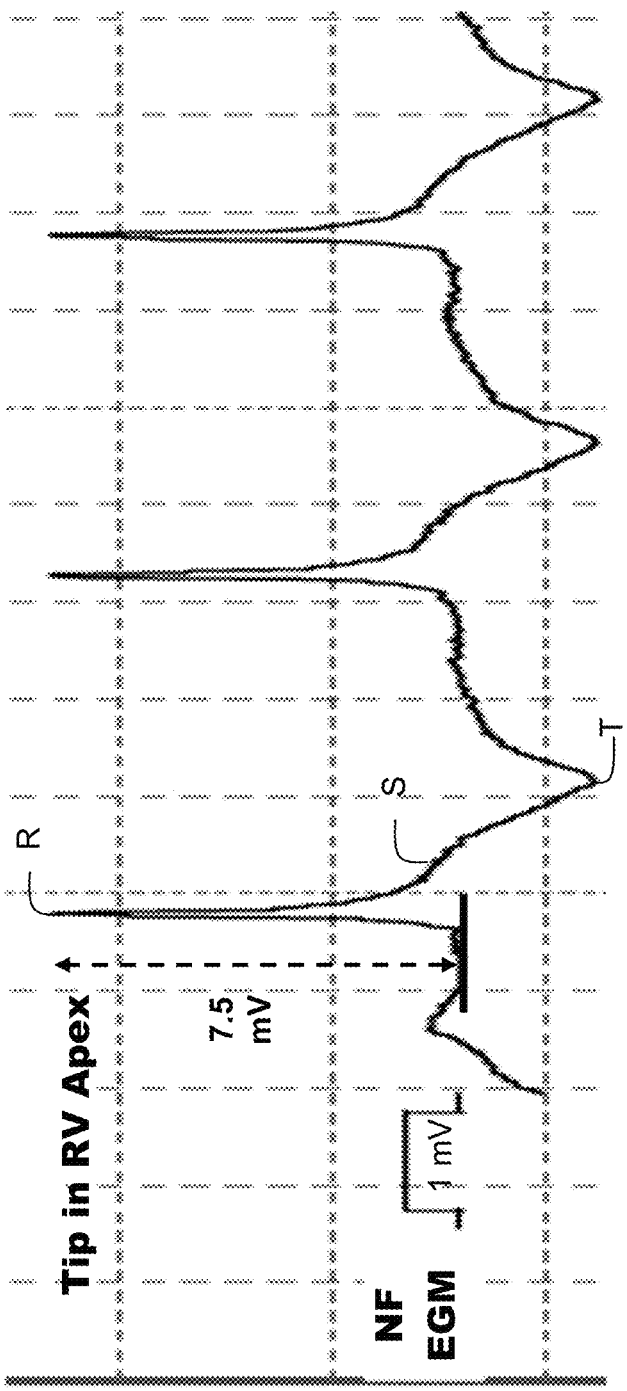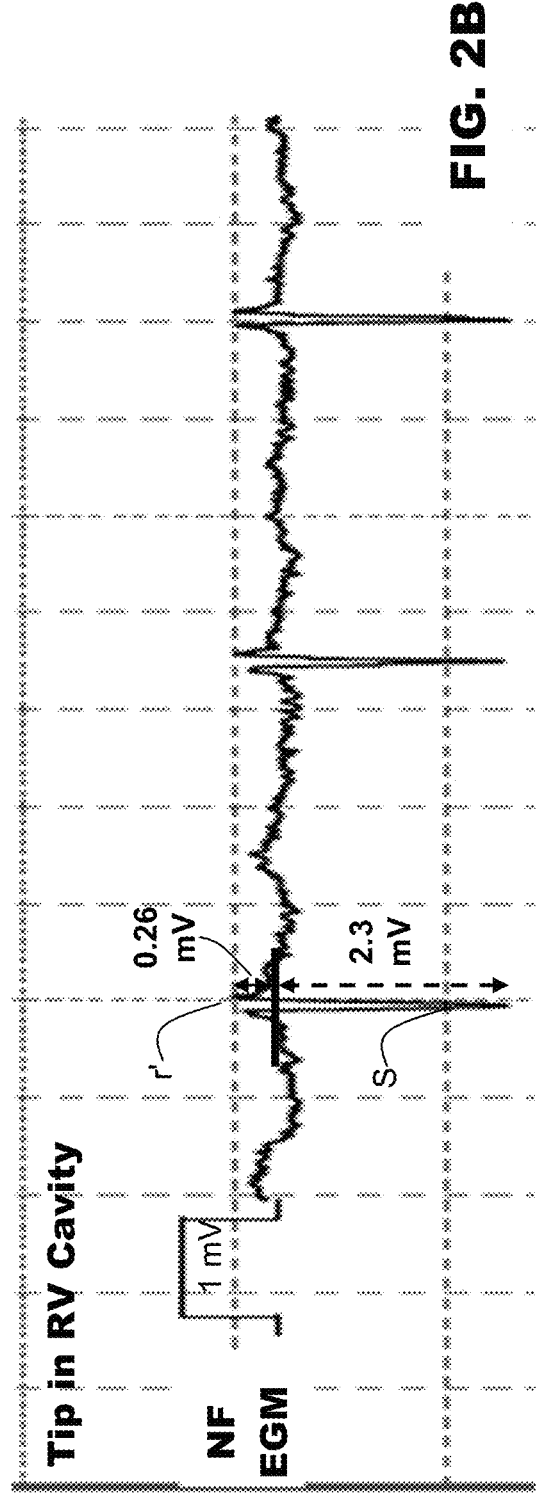

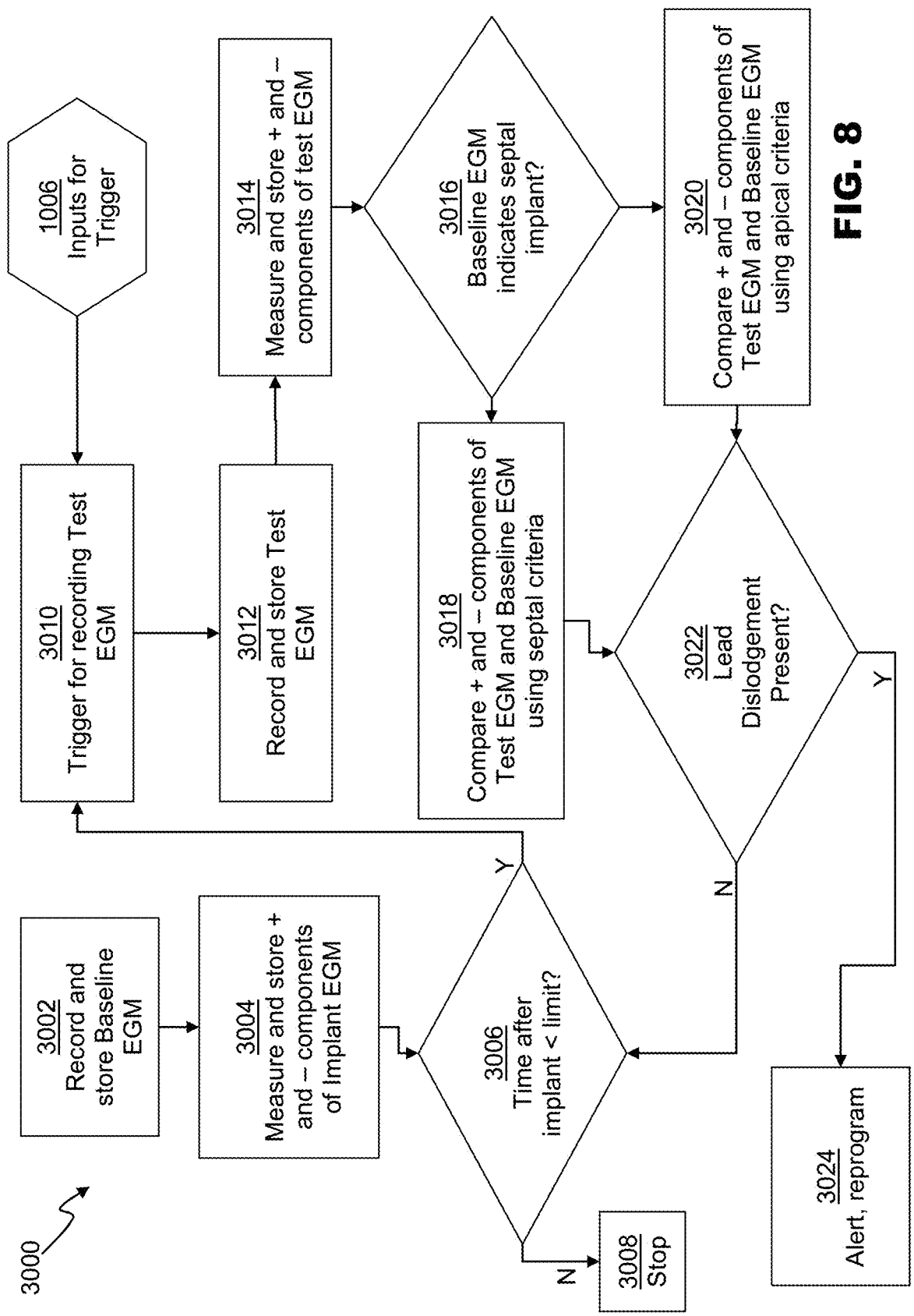

DETECTION OF LEAD ELECTRODE DISLODGEMENT USING CAVITARY ELECTROGRAM

RELATED APPLICATIONS

This application claims the benefit of U.S. Provisional Application No. 62/482,822 filed Apr. 7, 2017, the contents of which are incorporated by reference herein.

TECHNICAL FIELD

Embodiments of the present disclosure relate generally to the field of implantable medical devices. More particularly, the present disclosure relates to methods and systems for detecting dislodgement of a lead electrode associated with implanted medical devices such as an implantable cardioverter-defibrillator.

BACKGROUND

Implantable cardioverter-defibrillators (ICDs) are used to provide various types of therapy to a cardiac patient, including, for example cardioversion and/or defibrillation. These devices consist of a hermetic housing implanted into a patient and connected to one or electrodes, combinations of which can define low-voltage therapy (pacing) vectors, high-voltage therapy (defibrillation) vectors, and/or sensing vectors. The housing of the ICD contains electronic circuitry for monitoring the condition of the patient's heart, usually through sensing electrodes, and also contains a battery, high voltage circuitry and control circuitry to generate, control and deliver the defibrillation shocks. Typically, one or more leads are connected to circuitry within the ICD and to one or more defibrillator electrodes proximate the heart. One example of an ICD is disclosed in U.S. Pat. No. 5,405,363 to Kroll et al., the disclosure of which is hereby incorporated by reference.

Dislodgement of a right ventricular (RV) transvenous defibrillation lead, for example, is a rare complication of ICD therapy. However, such dislodgement deserves attention out of proportion to its low incidence because lead dislodgement may cause fatal proarrhythmia if the lead enters the right atrium, even in a patient having a normal, physiological, sinus rhythm. For example, a patient having an ICD may exercise and increase the heart rate to 120 beats-per-minute (bpm) corresponding to an R-R interval of 500 ms and a P-R interval of 200 ms. Both the P-waves and the R-waves are sensed with alternating P-R and R-P intervals of 200 ms (equivalent to 300 bpm) and 300 ms (equivalent to 200 bpm), resulting in erroneous detection of ventricular fibrillation (VF) by the ICD.

In response to such an erroneous detection of VF, a shock synchronized to the atrial electrogram (EGM) will likely be delivered by the ICD during the ventricular vulnerable period, 300 ms after the preceding R-wave. In a typical case, the vector of this shock is from the defibrillation electrode coil on the right ventricular (RV) lead to the housing or can of the ICD. But because the RV lead has dislodged, the defibrillation electrode coil of the RV lead is now likely positioned within the right atrium. This vector is sufficient for cardioversion of atrial fibrillation, but not for ventricular defibrillation. Thus, the shock will likely be below both the ventricular upper limit of vulnerability, and the defibrillation threshold for this shock vector. Because of this, the shock has a high likelihood of inducing VF that the ICD cannot either sense or defibrillate due to the dislodgement of the RV lead.

In another circumstance, dislodgement of a transvenous ICD lead into the atrium may cause fatal proarrhythmia in a patient experiencing atrial fibrillation (AF). For example, the high rate of an AF can sometimes be falsely classified by the ICD as VF. In response, a shock synchronized to the atrial electrogram will likely be delivered by the ICD during the ventricular vulnerable period. The vector of this shock is from the coil on the RV lead to the housing or can of the ICD. But because the RV lead has dislodged, the coil of the RV lead is now likely positioned within the right atrium. Because the shock vector is inefficient (right atrium to ICD housing or "can"), the shock's strength will likely be below both the ventricular upper limit of vulnerability and the ventricular defibrillation threshold. Thus, the shock has a high likelihood of inducing VF that the ICD cannot defibrillate. A related risk in this situation may occur if the inappropriate shock from the dislodged RV lead successfully defibrillates (cardioverts) the atrium. If the ICD then senses only the atrial signals of normal rhythm from its ventricular sensing electrode on the dislodged RV lead, the ICD will classify the shock as successful and, despite the potential for a related or separate VF occurring, the ICD would not deliver another shock. The result will then be a fatal, untreated VF.

Lead dislodgement to the atrium presents a significant risk even if no inappropriate shock is delivered because the ICD is unlikely to defibrillate spontaneous VF with a shock vector based on the dislodged lead. Further, lead dislodgement within the ventricle presents a serious complication even if the lead does not reach the atrium: A transvenous lead with the tip dislodged and free to move about within the RV cavity may induce ventricular tachycardia or VF by mechanical trauma. Additionally, such a dislodged lead does not provide reliable ventricular sensing, bradycardia pacing, or antitachycardia pacing.

Presently, no ICD has implemented any proposed method or algorithm to consistently and effectively detect or mitigate lead electrode dislodgement. U.S. Pat. No. 9,572,990 to Gunderson ("the '990 Patent"), teaches an algorithm that withholds therapy in sinus rhythm based on an anticipated pattern of electrical signals on the ventricular near-field (NF) electrogram. As used in ICDs, the near-field electrogram ventricular is recorded from two closely-spaced electrodes near the tip of the lead, at least one of which is a small sensing electrode at the tip of the lead. Because these electrodes are closely spaced, their electrical "field of view" is short-range and dominated by the electrical signals originating in myocardium adjacent to the lead tip. The near-field electrogram is thus ideal for sensing local myocardial electrical activity, and all ICDs monitor the near-field electrogram continuously for the purpose of sensing the cardiac rhythm.

The '990 Patent teaches detection of lead dislodgement to the atrium by the recording of short-long-short-long (S-L-S-L) sequences of intervals between near-field electrogram signals. The "short" interval corresponds to the P-R interval; the "long" corresponds to the R-P interval. Additionally, the algorithm requires that each signal have a relatively low amplitude (e.g., 0.5-2.5 mV) and that a zero crossing occurs in the short interval to exclude R-wave double-counting. This algorithm alerts when two such sequences occur. Unfortunately, the sensitivity of this pattern for lead dislodgement to the atrium is unknown, and this algorithm cannot detect lead dislodgement until the lead tip enters the atrium.

Additionally, the algorithm described in the '990 Patent is not effective under a number of lead dislodgement to the atrium conditions that do not result in S-L-S-L sequences on the near-field electrogram. One example occurs when the atrial rhythm is AF so there are multiple atrial EGMs for each ventricular EGM. Other examples relate to the limited "field of view" near-field electrogram. Because this field of view is restricted to local myocardial electrical signals, it does not reliably record signals from two cardiac chambers (atrium and ventricle) simultaneously during the unpredictable conditions of lead dislodgement to the atrium. Further, the method of the '990 Patent cannot detect lead dislodgements in which the lead tip remains in the ventricle and does not reach the tricuspid valve because in this case, the near-field electrogram records a ventricular signal but no atrial signal.

In contrast to a near-field electrogram, a far-field electrogram is an EGM recorded by one or more electrodes located at a distance from the source of the EGM. A ventricular far-field electrogram records ventricular activation using at least one electrode that is not in a ventricle. As used in ICDs, the ventricular far-field electrogram usually refers to an EGM recorded between two or more large, widely-spaced electrodes, used to deliver defibrillation shocks, at least two of which have opposite polarity during the shock and are thus separated in space by a distance of 10 cm or more.

U.S. Patent Pub. No. 2016/0375239 to Swerdlow ("the '239 Application"), the disclosure of which is incorporated by reference herein, proposes, inter alia, diagnosing lead dislodgement using measurements made on the far-field electrogram including absolute amplitude changes and occurrence of the S-L-S-L pattern. This overcomes some limitations of the '990 Patent, for diagnosis of lead dislodgement to the atrium.

Methods are known in the art for the diagnosis of dislodgements of leads other than RV leads. For example, U.S. Pat. No. 5,713,932 to Gillberg et al. discloses a method of diagnosing atrial lead dislodgement to the ventricle limited to patients who have intact atrioventricular conduction. Atrial lead dislodgement to the ventricle is diagnosed if the atrial lead is paced and the interval from the atrial pacing pulse to the ventricular near-field electrogram is less than the expected delay from atrioventricular conduction. U.S. Pat. No. 7,664,550 to Eik et al. discloses a method for diagnosing dislodgement of left-ventricular lead placed within a venous branch of the coronary sinus. This method involves difference in waveforms related to larger atrial and smaller ventricular signals when the lead dislodges. Similarly, U.S. Pat. No. 9,327,131 to Ryu et al. discloses a method for diagnosing dislodgement focused on left-ventricular leads based on the relative amplitude of atrial and ventricular signals.

A need remains, therefore, for improved methods and systems of detecting lead electrode dislodgement.

SUMMARY

Embodiments of the present disclosure provide improved methods and systems of detecting dislodgement of an electrode fixed to the endocardium of a cardiac chamber when in situ. The detection of electrode dislodgement is based on recognizing a cavitary electrogram as a characteristic pattern of polarity change, or polarity and amplitude change, recorded by an electrogram in which one of the recording electrodes is in contact with the endocardium when in situ. Cavitary electrograms can be recognized as soon as the relevant electrode is dislodged from the endocardium or wall of the chamber and enters the cavity of that chamber.

Embodiments of the current disclosure can be used, for example, to diagnose dislodgement of a transvenous defibrillation lead while the lead tip and most or all of the defibrillation electrode coil remain free in the cavity of a chamber of the heart, such as the right ventricle (RV), before the lead enters another chamber of the heart. Embodiments of the current disclosure can also be used to diagnosis dislodgement of other medical devices and peripherals (including leadless capsule defibrillators or other implantable leads) that include at least one electrode that is intended to be in contact with the wall of a chamber of the heart. For example, embodiments can be used to diagnose dislodgement of a leadless capsule pacemaker while the capsule remains in the cavity of the chamber of the heart.

Embodiments provide a method and system of identifying dislodgement of an electrode, operably coupled to an implanted electronic device, from fixation with the endocardium of a chamber of the heart of a patient. Various embodiments can include obtaining a test electrogram, determining at least two parameters of the test electrogram indicative of fixation of the electrode with the endocardium, and determining whether a cavitary electrogram is indicated based on the at least two parameters. In embodiments, the determination can be performed by a processor within the implanted electronic device. When a cavitary electrogram is indicated, at least one action can be performed. In embodiments, the action can include generating an electrode dislodgement alert and/or changing the configuration or programming of the implanted medical device to disable sensing and/or therapy.

In embodiments, the at least two parameters can include a test positive component magnitude based on the absolute magnitude of the greatest positive component of the test electrogram, and a test negative component magnitude based on the absolute magnitude of the greatest negative component of the test electrogram.

Embodiments can further comprise determining whether a cavitary electrogram is indicated based on the test positive component magnitude and the test negative component magnitude.

In certain embodiments, the detection is performed for only a predetermined amount of time following the implantation of the electronic device. The predetermined amount of time can be less than or equal to six months, or more preferably about three months.

In embodiments, the test electrogram is obtained at predetermined time intervals after implant. The test electrogram can also be triggered to be obtained in response to one or more of: a sufficient decrease in the rectified amplitude of the sensing electrogram which is measured periodically, a sufficient increase in the pacing threshold, which is measured periodically, and a sufficient decrease in pacing impedance, which is measured periodically.

In embodiments obtaining the test electrogram comprises recording the electrogram and storing the electrogram a memory of the implanted electronic device. In embodiments, the chamber of the heart is selected from the group consisting of: the right ventricle of the heart, the right atrium of the heart, the left ventricle of the heart, and the left atrium of the heart.

In embodiments, a cavitary electrogram can be indicated based on one or more criteria. For example, a cavitary electrogram can be indicated when the test negative component magnitude exceeds the test positive component magnitude by a predetermined threshold, which can be zero.

In embodiments, a cavitary electrogram can be indicated when the ratio of the test negative component magnitude to the test positive component magnitude is greater than a pre-specified absolute or relative value.

In embodiments, a cavitary electrogram can be indicated when the test positive component magnitude is less than a predetermined value, which can be between about 1 mV and about 3 mV In embodiments, a cavitary electrogram can be indicated when the test negative component magnitude is greater than a predetermined value, which can be between about 1 mV.

In embodiments, a cavitary electrogram can be indicated when the test negative component magnitude is within a predetermined range which can be between about 1 mV and about 5 mV, or between about 1 mV and 3 mV.

In embodiments, a cavitary electrogram can be indicated when the ratio of the test negative component magnitude to the test positive component magnitude is greater than a predetermined value, the absolute test negative component magnitude is within a prespecified negative component range, and the absolute value magnitude of said positive component is within a prespecified positive component range. In embodiments, the predetermined value can be one, the negative component range can be between about 1 mV to about 5 mV, and the prespecified positive component range can be between about 0 mV and about 2 mV.

In embodiments, the method and systems can further comprise obtaining a baseline electrogram at a time before obtaining the test electrogram, measuring a baseline positive component magnitude based on the absolute magnitude of the greatest positive component of baseline electrogram, and measuring a baseline negative component magnitude on the absolute magnitude of the greatest negative component of one or more baseline electrograms. Electrode dislodgement can be further determined based on absolute or relative differences between the baseline electrogram and the test electrogram with respect to positive component magnitude and/or negative component magnitude.

In embodiments, a cavitary electrogram can be indicated when the absolute ratio of the test negative component magnitude to the baseline negative component magnitude is greater than or equal to a predetermined ratio, such as greater than or equal to three.

In embodiments, the method and system can further comprise calculating a first ratio of the baseline positive component magnitude to the baseline negative component magnitude, and calculating a second ratio of the test negative component magnitude to the test positive component magnitude. A cavitary electrogram can be indicated when the first ratio exceeds a first predetermined threshold and the second ratio exceeds a second predetermined threshold. Electrode dislodgement can also be determined to have occurred when the product of the first ratio and the second ratio exceeds a predetermined threshold.

Infrequently, the negative component of the baseline electrogram may have a large relative or absolute value. This may occur when a RV endocardial lead is implanted on the interventricular septum. In embodiments, the baseline electrogram can be analyzed to determine if the negative component of the baseline electrogram exceeds a relative or absolute value suggesting that alternative criteria can be used to determine if a cavitary electrogram is indicated. In an embodiment, if the baseline positive component magnitude is greater than 1 mV, the baseline negative component magnitude is greater than 3 mV, and the baseline positive component magnitude is less than the baseline negative component magnitude alternative criteria can be used. For example, a cavitary electrogram can be indicated when the test positive component magnitude is either less than 1 mV of less than the value of the baseline positive component magnitude by an absolute or relative difference, the test negative component magnitude is less than 5 mV, and the test positive component magnitude is less the test negative component magnitude.

Embodiments include a method and system of identifying dislodgement of an electrode that is operably coupled to an implanted electronic device from the endocardium of a chamber of the heart of a patient. The electrode can be situated in or on a lead, or a capsule type electronic device such as a leadless, capsule pacemaker. One or more near-field or unipolar test electrograms can be obtained. A processor within the implanted electronic device can be used to measure a magnitude of a positive component based on the absolute magnitude of the greatest positive component of the one or more near-field test electrograms and a magnitude of a negative component based on the absolute magnitude of the greatest negative component of one or more said near-field electrograms. The dislodgement of the electrode from fixation in the endocardium can be determined based on the test positive component magnitude, the test negative component magnitude, and one or more criteria. When dislodgement has been determined, an alert can be generated to indicate that the electrode has dislodged.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures.

FIG. 2A is a digitally-stored, real-time recording depicting a near-field electrogram recorded with the lead tip in situ at the RV apex.

FIG. 2B is a digitally-stored, real-time recording depicting a near-field electrogram recorded with the lead dislodged to the RV cavity.

FIG. 8 is a flowchart depicting detection of an electrode dislodgment, according to an embodiment.

Figure 1B:
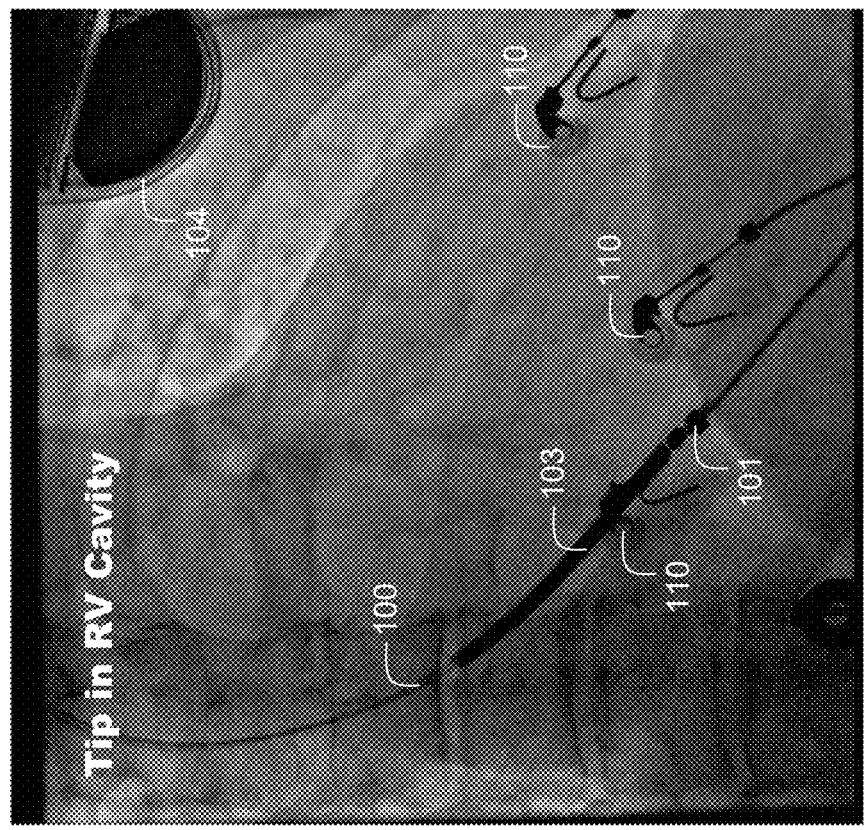
FIG. 1B is a right anterior oblique cinefluoroscopic images recorded at ICD implant of an ICD lead dislodged to the right ventricular cavity of the patient.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Embodiments relate to a method and system for detecting dislodgement of an electrode of an implantable medical devices, such as a tip electrode of an ICD transvenous lead, from fixation within the endocardium of a chamber of the heart of a patient. Embodiments of the present disclosure enable detection of electrode dislodgment, and therefore the terms lead electrode dislodgement, electrode dislodgement, and lead dislodgement may be used interchangeably herein, depending upon the embodiment of the electrode being discussed.

Figure 1A:
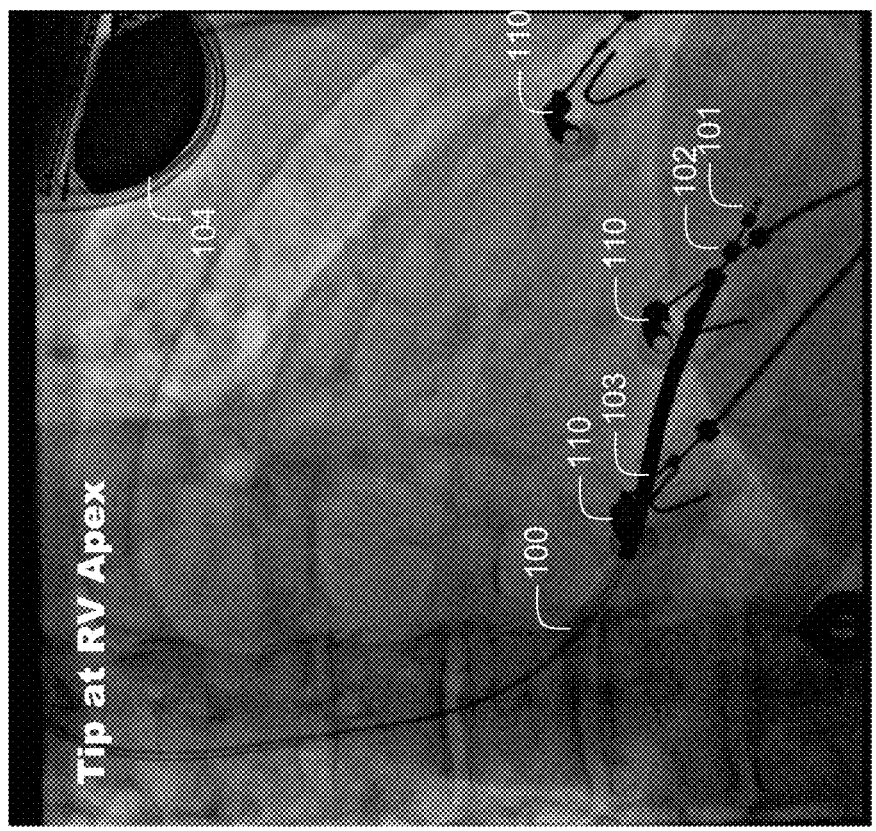
FIG. 1A is a right anterior oblique cinefluoroscopic images recorded at ICD implant of an ICD lead in electric contact with the endocardium at the apex of the right ventricle of the patient.

FIGS. 1A and 1B depict right anterior oblique cinefluoroscopic images recorded at ICD implant during a simulated dislodgement of a typical transvenous ICD lead. The lead 100 connects to a pulse generator 104, which can be an ICD, pacemaker, or other implantable electronic device. The pulse generator 104 can be positioned in a prepectoral pocket. The lead 100 comprises a tip electrode 101, a ring electrode 102, a defibrillation electrode or shock coil 103, and other components including conductors and connectors connecting the electrodes and coil to the pulse generator and various layers of insulation material. Other lead or leadless electrode configurations can be used in embodiments. FIG. 1A depicts the tip electrode 101 in contact with the endocardium of the RV. FIG. 1B depicts the tip electrode 101 dislodged from the endocardium of the RV and free within the RV cavity. FIGS. 1A and 1B also depict various surface electrocardiographic electrodes 110 that can be used to monitor to the patient during the implant procedure.

FIGS. 2A and 2B depict wide-band filtered, near-field electrograms recorded at the positions shown in FIGS. 1A and 1B, respectively, with 1 mV calibration markers. Here, the depicted near-field electrograms are dedicated-bipolar electrograms recorded between the tip electrode 101 and ring electrode 102. However, those of ordinary skill in the art will appreciate that near-field can also refer to an integrated-bipolar electrogram recorded between the tip electrode 101 and the shock coil 103.

The narrow field of view provided by a bipolar sensing electrogram recorded from a near-field sensing bipole can provide electrograms that are sensitive to loss of contact between the sensing electrode and the endocardium or heart wall. A unipolar sensing bipole recorded between an electrode in contact with the endocardium and a remote electrode is also sensitive to contact between the tip electrode and endocardium. It will therefore be understood that the cavitary electrogram techniques described in the present disclosure are applicable to any electrogram in which one of the two recording electrodes is in direct contact with the myocardium and/or endocardium when the system component containing the electrode—such as a pacing lead, defibrillation lead, or leadless capsule pacemaker, is actively or passively fixated in-situ. Thus, while embodiments of the present disclosure are discussed in terms of near-field electrograms, those of ordinary skill in the art will appreciate that embodiments are also applicable to unipolar electrograms recorded between the tip electrode 101 and a remote electrode such as the ICD housing.

FIG. 2A depicts an electrogram recorded with the tip electrode 101 in contact with the RV apex corresponding to the lead position depicted in FIG. 1A. The electrogram of FIG. 2A has a "dominant R" shape, with a large positive component (as depicted by the 7.5 mV magnitude of the R wave, 7.5 mV) and no negative component.

FIG. 2B depicts an electrogram recorded with the tip electrode 101 pulled back to the RV cavity, corresponding to the lead position in FIG. 1B. This cavitary electrogram has an rSr' triphasic shape: a small initial positive component (r, 0.21 mV, not shown), a large negative component (S, 2.3 mV), and a small terminal positive component (r', 0.26 mV).

As can be seen, dislodgement of the electrode tip of the transvenous lead into the RV cavity resulted in a an electrogram polarity change with a marked decrease in the electrogram's positive component (7.5 to 0.26 mV, a 97% decrease), and the appearance of a dominant negative component (0.0 to 2.3 mV). An R/S ratio can be calculated based on the absolute value of the magnitude of the R and S waves. In the electrogram of FIG. 2A, the R/S ratio is >10 (7.5/~0), while the R/S ratio is 0.11 (0.26/2.3) in the electrogram of FIG. 2B.

Figure 3A:
FIG. 3A is a pair of digitally-stored, real-time recordings depicting near-field electrograms recorded with the lead tip in situ at the RV apex, and the lead tip dislodged to the RV cavity.
Figure 3B:
FIG. 3B is a pair of digitally-stored, real-time recordings depicting near-field electrograms recorded with the lead tip in situ at the RV apex, and the lead tip dislodged to the RV cavity.
Figure 3C:
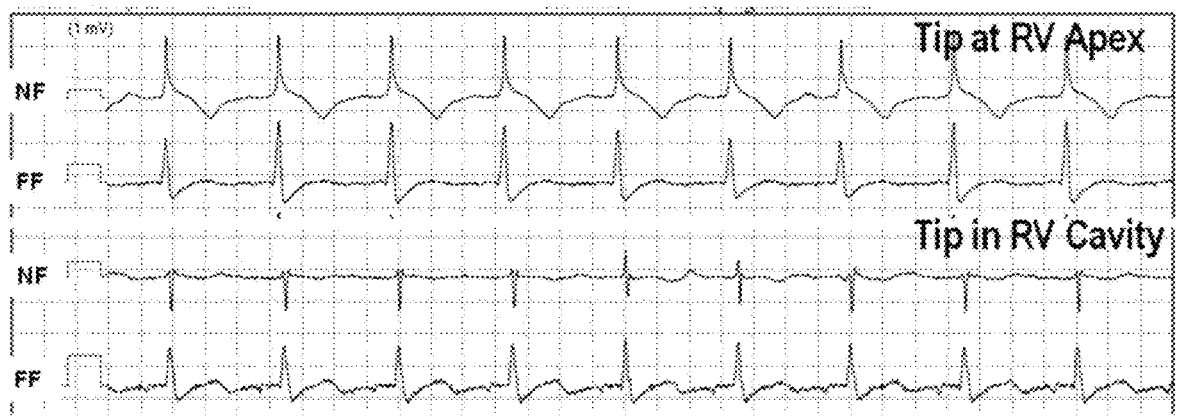
FIG. 3C is a pair of digitally-stored, real-time recordings depicting near-field electrograms recorded with the lead tip in situ at the RV apex, and the lead tip dislodged to the RV cavity.

FIGS. 3A-3C depict additional examples recorded during simulated dislodgement of an ICD lead in three other patients. In each of FIGS. 3A-3C, the upper tracings show electrograms recorded with the tip touching the RV apex, and the lower tracings show electrograms recorded with the tip free in the RV cavity. In each pair, the upper tracing is the near-field electrogram (NF) and the lower tracing is the far-field electrogram (FF) recorded between the RV coil and ICD can.

As can be seen, each panel shows the same, consistent pattern change in near-field electrogram, from a dominant positive component with the tip at the RV apex to a dominant negative component with the tip in the RV cavity. Additionally, each panel shows both a reduction in the absolute value of the positive component and an increase in the absolute value of the negative component.

Figure 4:
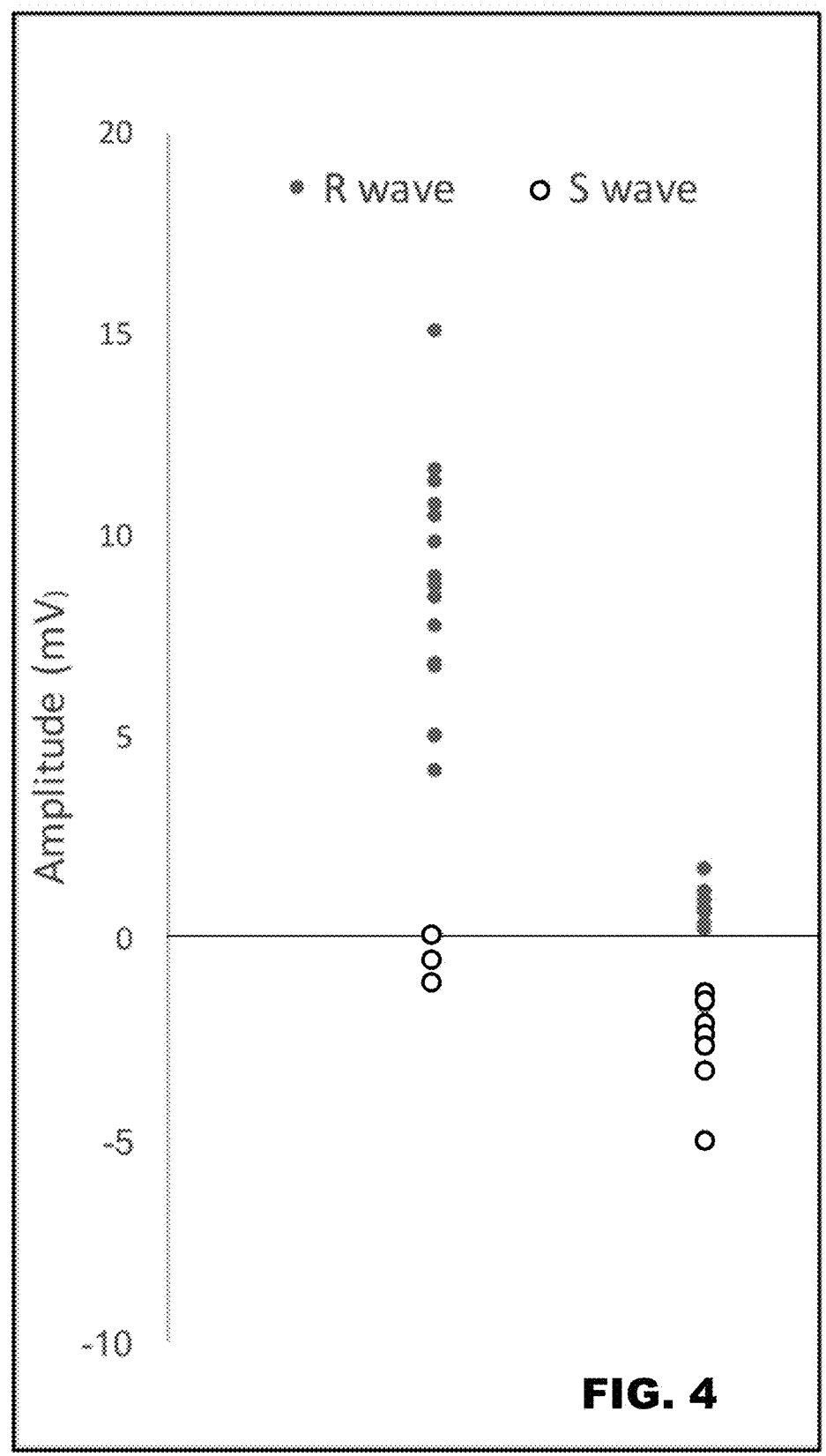
FIG. 4 is a graphical view of the amplitude of measured R and S waves.

FIG. 4 is a graphical representation of R and S wave amplitudes recorded during experimental lead dislodgements in 15 patients during ICD implant. The cardiac rhythm was sinus in 12 patients, atrial fibrillation in 2 patients, and atrial flutter in 1 patient. Each patient gave written, informed consent to a protocol approved by the Committees on Human Research. In the implanted position, positive R waves ranged from 4.1 to 15.1 mV and negative S waves from 0.0-1.2 mV. In contrast, with the lead tip in the RV cavity, positive R waves ranged from 0.3-1.7 mV and negative S waves from 1.3-5.0 mV. In all 15 patients, the R-wave amplitude decreased and the S wave amplitude increased as the lead dislodged from the implanted position to the position with the tip free in the RV cavity. In all patients, the R/S ratio exceeded 1.0 with the tip implanted at the RV apex and was less than 1.0 with the tip free in the RV cavity.

Figure 5:
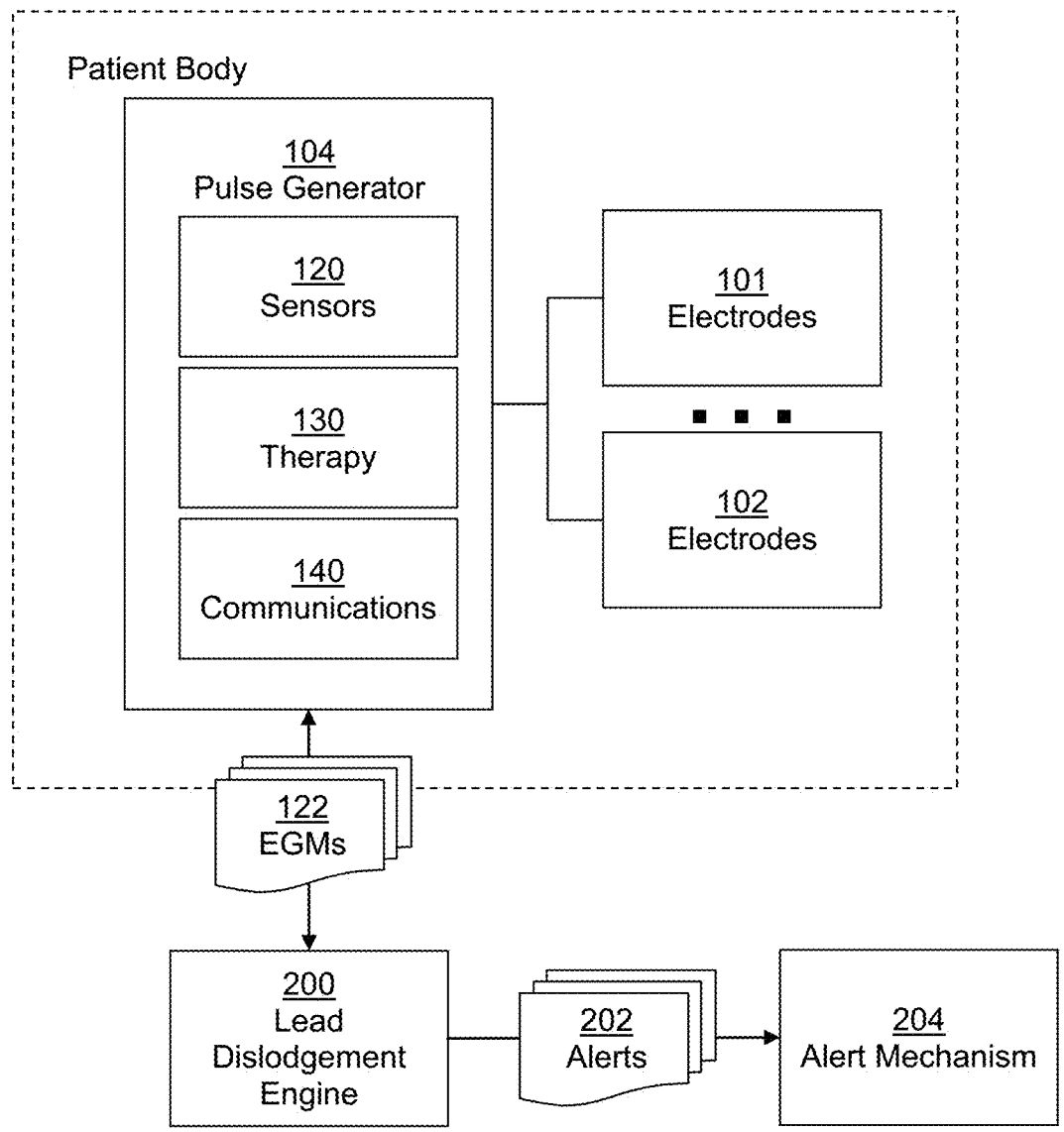
FIG. 5 is a block diagram depicting a schematic view of a lead electrode dislodgement detection system, according to an embodiment.

FIG. 5 is a block diagram depicting an implantable cardiac device, such as pulse generator 104, in context with a lead dislodgement engine 200. Those of ordinary skill in the art will appreciate that typical pulse generators 104 can comprise sensors 120 and therapy generators 130 of various configurations, that are operably coupled to one or more electrodes, such as a tip electrode 101, ring electrode 102, and other therapy electrodes. Typical pulse generators 104 further generally comprise a communications module 140, capable of wired or wireless telemetry with one or more external devices, such as programmer recorder monitors. Lead dislodgement engine can comprise software and/or hardware components configured to detect dislodgement of a lead from fixation within the endocardium of the heart of the patient based on electrogram data 122 received from sensors 120.

In embodiments, all or parts of lead dislodgement engine 200 can reside in the processor and memory of pulse generator 104. In alternative embodiments, all or parts of lead dislodgement engine 200 can reside on one or more external computer systems, such as a programmer recorder monitor, or independent computer, smart phone, or table. In general, therefore, lead dislodgement engine 200 can reside in any electronic device, in any form, in any location, provided that lead dislodgement engine 200 can receive electrogram data 122, and provide alerts 202 to patients, clinicians, or other caregivers via alert mechanism 204. In one embodiment, for example, lead dislodgement engine 200 can reside entirely within pulse generator 104, and receive electrogram data 122 directly from sensors 120. If lead dislodgement is detected, lead dislodgement engine 200 can signal a lead dislodgement alert 202 via the pulse generators internal alert system. For example, a lead dislodgement alert can be put on a message queue, and a beeper or other audible alert signal can be activated by the pulse generator 104.

In another embodiment, lead dislodgement engine 200 can reside on an external programming device. Electrogram data 122 can be received via telemetry communications from pulse generator 104. Lead dislodgement engine 200 can comprise a user interface configured to provide the user with information based on lead dislodgement detection activities. The user interface can receive user inputs and provide user outputs regarding configuration of lead dislodgement engine 200 and the detection of lead dislodgement. The user interface can comprise a mobile application, web-based application, or any other executable application framework. The user interface can reside on, be presented on, or be accessed by any computing device capable of communicating with the various components of lead dislodgement engine 200 and pulse generator 104, receiving user input, and presenting output to the user. In embodiments, the user interface can reside or be presented on a smartphone, a tablet computer, laptop computer, or desktop computer.

In operation, lead dislodgement can be detected by examination of the positive and negative components of electrograms recorded by an implanted electronic device such as an ICD. Because most lead dislodgements occur within a few months of lead implant, lead dislodgement can be deactivated after a period of time post-implant. This can reduce unnecessary battery drain or memory use, as well as lowering the risk of false positive determinations of dislodgement. In embodiments this limit can be about one year, about six months, or about three months, though other limits can be used. In embodiments, the limit can be user configurable.

Figure 6:
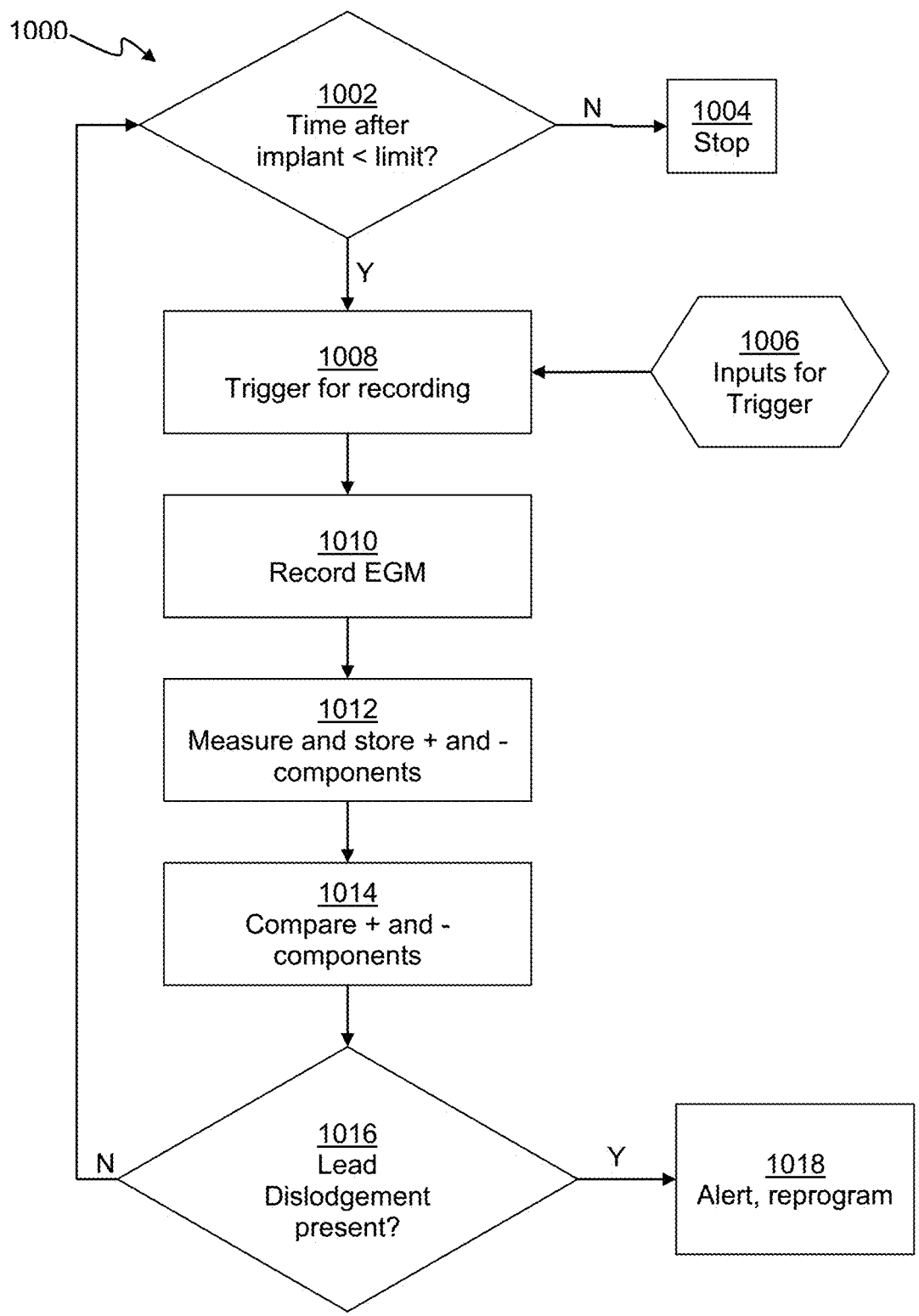
FIG. 6 is a flowchart depicting detection of an electrode dislodgment, according to an embodiment.

FIG. 6 is a flowchart depicting an embodiment of a method 1000 for detecting lead dislodgement based on a recorded test electrogram. At 1002, the time after implant can be compared to a configured limit. If the time after implant has elapsed, execution can stop at 1004. Stopping execution at 1004 can also comprise disabling any triggers that were previously activated by method 1000.

If the time after implant is less than the limit, then various inputs 1006 may activate the trigger 1008 for recording one or more test electrograms. Optionally, one or more other electrograms can be stored, such as a far-field electrogram. Inputs 1006 can include one or more timers (for example, method 1000 can be executed once per day), or cardiac activity patterns (such as changes in beats per minute or lead impedance) or any other inputs. Trigger inputs can also include threshold values of periodically measured lead performance metrics (R-wave amplitude, pacing threshold, or pacing lead impedance), or relative or absolute changes in these values with respect to a baseline.

At 1010 the test electrogram can be recorded. In embodiments, the test electrogram can be recorded for a duration of time, a number of cardiac cycles, or for any other period.

At 1012 the electrogram is stored, the absolute value of the positive and negative components are measured. In embodiments, a test positive component magnitude can be measured based on the absolute magnitude of the largest positive magnitude (maximum voltage) of the test electrograms, and a magnitude of a negative component can be measured based on the absolute magnitude of the largest negative magnitude (minimum voltage) of the test electrograms. The amplitude of positive and negative components of the test electrograms can be measured by any method commonly used for automated electrogram measurement in pacemakers or ICDs, except that the signal is not rectified before the measurement is performed. In this disclosure, "positive" is defined as the polarity of the largest deflection for a lead tip in contact with the RV apex. This convention is meant to simplify discussion and claims as an amplifier might also produce the opposite polarity. The greatest positive component may also be referred to as the "R wave" and the greatest negative component as the "S wave" In embodiments, if the amplitude of the positive component is below the measurement threshold of the pulse generator, the positive amplitude can be assigned to zero, or to the measurement threshold. For example, if the sensing threshold is 0.3 mV, and the positive amplitude is 0.1 mV, the positive amplitude can be set to zero or 0.3 mV, the latter of which can avoid dividing by zero when calculating an S/R ratio.

At 1014 these components are compared, and a determination of electrode dislodgement is made in relation to this comparison. Electrode dislodgement can be determined by detecting whether the test electrogram(s) are cavitary electrograms. A cavitary electrogram in accordance with various embodiments can be an electrogram that meets one or more of several determination criteria.

The determination criteria can include whether the amplitudes of the positive and negative components are greater than or less than absolute or relative thresholds. In embodiments, relative thresholds can be determined in relation to the value of the positive and/or negative amplitudes at implant, or at a time between implant and the execution of method 1000.

The determination criteria can further include whether the absolute value of the negative amplitude exceeds the absolute value of the positive amplitude by a predetermined value. In exemplary embodiments, the relationship of the positive and negative amplitudes can be expressed as differences or ratios.

In embodiments in which the electrode is a tip electrode on a transvenous lead, for example, a lead dislodgement can be diagnosed if all of the following are true: the positive component less than an absolute threshold of 3 mV, the negative component is greater than an absolute threshold of 1 mV and less than an absolute threshold in the range of 3-5 mV, and ratio of negative component to positive component is greater than one. Alternatively, lead dislodgement may be determined if a plurality of criteria are met.

In embodiments, a lead dislodgement can be diagnosed if both of the following are true: the positive component less than an absolute threshold of 1 mV and the ratio of the negative component to positive component is greater than one.

At 1016, if lead dislodgement is determined, at 1018 a lead-dislodgement alert can be generated and/or the pulse generator 104 can be reprogrammed and/or reconfigured to suspend detection of, or therapy in response to ventricular fibrillation and ventricular tachycardia. In embodiments, the generation of an alert can comprise storing a representative electrogram (such as the test electrogram), sending a remote-monitoring alert that is transmitted electronically via the implantable device internet-based, remote-monitoring network (if available), and/or a patient alert that can be in or more forms such as an audible tone or vibration. If no lead dislodgement is determined, control can return to 1002.

Figure 7:
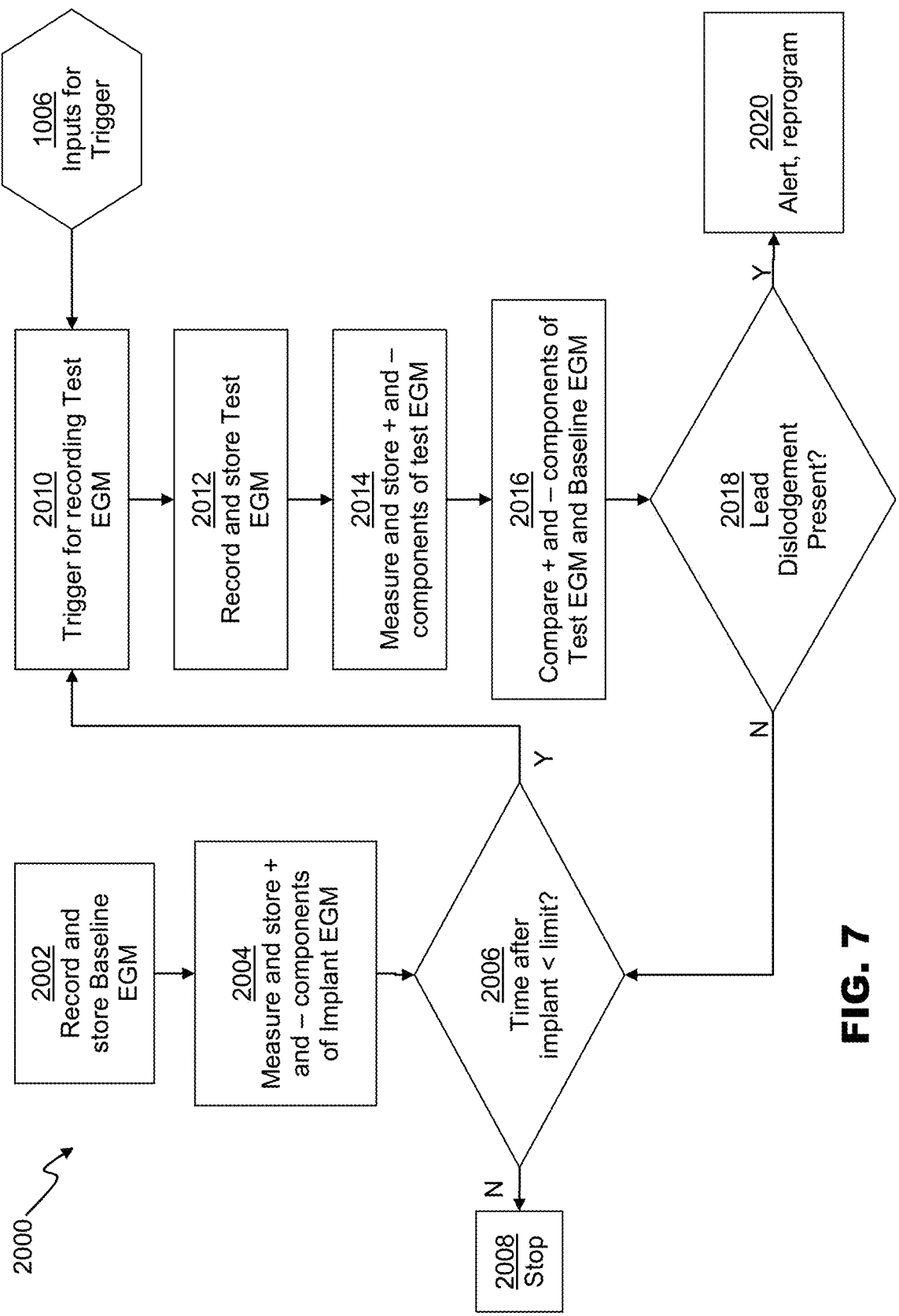
FIG. 7 is a flowchart depicting detection of an lead electrode dislodgment, according to an embodiment.

FIG. 7 is a flowchart depicting an embodiment of a method 2000 for detecting lead dislodgement based on a both a baseline electrogram and a test electrogram. At 2002, a baseline electrogram can be recorded and stored. Optionally, one or more other electrograms can be stored, such as a far-field electrogram. Also, optionally, the baseline electrogram can be updated periodically, so long as electrical measurements of lead performance—such as pacing threshold, automatically-measured rectified R-wave amplitude, and pacing impedance—remain within a predefined narrow range. The baseline electrogram can be recorded at implant or shortly after implant at a prespecified time (e.g. one to twenty-four hours). Alternatively, the baseline electrogram can be recorded for the first time at or immediately after implant, and updated periodically providing that periodically measured lead performance metrics (R-wave amplitude, pacing threshold, or pacing lead impedance) are stable in comparison with their own baseline values. At 2004, the amplitudes of its positive and negative components can be measured and stored, in the same or similar manner as the test electrogram components discussed with reference to 1012 above.

At 2006, the time after implant can be compared to a configured limit. If the time after implant has elapsed, execution can stop at 2008. If the time after implant is less than the limit, then the various inputs 1006 (discussed above) can activate the trigger at 2010 for recording one or more near-field test electrograms at 2012. Optionally, one or more other electrograms can be stored, such as a far-field electrogram. At 2014, the positive and negative components can be measured and stored in the same or similar manner as discussed with reference to 1012 above.

At 2016, the occurrence of a lead dislodgement can determined by one or more relative or absolute changes in positive and negative electrogram components from the baseline electrogram to the test electrogram. Lead dislodgement can be determined by detecting whether one or more of several determination criteria are met.

The determination criteria can include whether the positive component of the test electrogram is less than a pre-specified percentage of the positive component of the baseline electrogram, for example 25%.

The determination criteria can further include whether the positive component of the test electrogram is both less than a threshold value, for example 3 mV, and less than a prespecified percentage of the positive component of the baseline electrogram, for example 50%

The determination criteria can further include whether the negative component of the test electrogram is greater than a prespecified multiple of the negative component of the baseline electrogram, for example 4 times.

The determination criteria can further include whether the positive component of the baseline electrogram is less than a prespecified value, for example 2 mV. The determination criteria can further include whether the negative component of the test electrogram exceeds a prespecified value, for example 1 mV.

At 2018, if lead dislodgement is determined, at 2020 a lead dislodgement alert can be generated and/or the pulse generator 104 can be reprogrammed or reconfigured as discussed with reference to 1018 above. Similarly, if no lead dislodgement is determined, control can return to 2006.

In embodiments, the specific determination criteria utilized can be determined based on the shape and size of the baseline electrogram, as indicated by the absolute and/or relative positive component value and negative component value of the baseline electrogram. For example, as seen in FIG. 4 the magnitude of the negative component of a baseline electrogram recorded at the RV apex is generally small, less than 1 mV. However, it is known in the art that the amplitude of the negative component of near-field electrograms recorded from leads that are in situ at the interventricular septum may be larger than the amplitude of the positive component. For electrograms of in situ leads with an electrode in a septal location, the positive component often exceeds 1 mV and the negative component often exceeds 3 mV.

FIG. 8 is a flowchart, depicting a method 3000 for detecting electrode dislodgement using criteria selected based on the baseline electrogram. Method 3000 is depicted and described in terms of septal and apical implant locations. Those of ordinary skill in the art will appreciate, however, that method 3000 can be adapted to enable selection of dislodgement detection criteria based on the configuration (in terms of polarity, amplitude, or other features) of the baseline electrogram. Like method 2000, described above, the baseline electrogram can be recorded and stored at 3002, and the components can be measured at 3004. If too much time has elapsed since implant at 3006, execution can be stopped at 3008. If execution continues, when a trigger 1006 for recording a test electrogram is received at 3010, the test electrogram can be recorded and stored at 3012, and the positive and negative components can be measured at 3014. As described in reference to method 2000, optionally additional electrograms can be recording, and/or the baseline electrogram can be updated at intervals, or upon request.

At 3016, however, the criteria used to compare the positive and negative components of the test electrogram and baseline electrogram can be chosen based on whether the baseline electrogram indicates that the lead was initially implanted in the septum. In embodiments, a septal lead location can be determined if the magnitude of the positive component is greater than 1 mV, the magnitude of the negative component is greater than 3 mV, and the magnitude of the positive component is less than the magnitude of the negative component.

If these criteria are met, then dislodgement can be determined using prespecified septal criteria at 3018. For example, electrode dislodgement can be determined if the test electrogram has a positive component magnitude less that is than the value of the baseline positive component, a negative component amplitude that is less than 5 mV and a positive component amplitude that is less than negative component amplitude.

If the baseline electrogram does not indicate that the lead was implanted at a septal location, alternative "apical" criteria, such as those described with respect to 2016 of method 2000 above, can be used at 3020.

At 3022, if electrode dislodgement is determined (either via septal criteria or apical criteria), actions can be taken at 3024. If not, control can return to 3006.

Those of ordinary skill in the art will appreciate that while the detection of dislodgement of a right-ventricular defibrillation lead is the primary example depicted and described herein, methods and systems of the present disclosure are applicable to dislodgement of an electrode attached to the endocardium of any cardiac chamber. This includes for example, dislodgement of electrodes attached to a right-ventricular pacing lead, a right-atrial pacing lead, or an endocardial leadless, capsule pacemaker.

Further, those of ordinary skill in the art will appreciate that the embodiments of the present disclosure provide a number of advantages over conventional lead dislodgement detection techniques. For example, embodiments of the present disclosure can be used to detect lead dislodgement at an earlier stage than conventional techniques allow. Further, embodiments of the present disclosure apply equally in sinus rhythm and atrial fibrillation because embodiments detect lead dislodgement based on changes that occur as soon as the tip electrode loses contact with the endocardium.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

In one embodiment, components and subsystems of lead dislodgement engine 200, and/or components or subsystems of other systems and devices discussed herein can include computing devices, microprocessors, modules and other computer or computing devices, which can be any programmable device that accepts digital data as input, is configured to process the input according to instructions or algorithms, and provides results as outputs. In one embodiment, computing and other such devices discussed herein can be, comprise, contain or be coupled to a central processing unit (CPU) configured to carry out the instructions of a computer program. Computing and other such devices discussed herein are therefore configured to perform basic arithmetical, logical, and input/output operations.

Computing and other devices discussed herein can include memory. Memory can comprise volatile or non-volatile memory as required by the coupled computing device or processor to not only provide space to execute the instructions or algorithms, but to provide the space to store the instructions themselves.

In one embodiment, the system or components thereof can comprise or include various modules or engines, each of which is constructed, programmed, configured, or otherwise adapted to autonomously carry out a function or set of functions. The term "engine" as used herein is defined as a real-world device, component, or arrangement of components implemented using hardware, such as by an application specific integrated circuit (ASIC) or field-10 programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Moreover, reference in the specification to "one embodiment," "an embodiment," or "some embodiments" means that a particular feature, structure, or characteristic, described in connection with the embodiment, is included in at least one embodiment of the teaching. The appearances of the phrase "in one embodiment" in various places in the specification are not necessarily all referring to the same embodiment.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. A method of identifying dislodgement of a lead from fixation with the endocardium of a chamber of the heart of a patient, the lead having an electrode being positioned proximate a distal tip of a lead that is configured for fixation with the endocardium of the chamber of the heart of the patient at implant of an implanted medical device, the electrode being operably coupled proximate a proximal end of the lead to an implanted medical device, the method comprising:
  obtaining a test electrogram for the electrode;
  using a processor to:
    determine at least two parameters of the test electrogram indicative of fixation of the electrode with the endocardium, wherein the at least two parameters include:
      a test positive component magnitude based on an absolute magnitude of a greatest positive component of the test electrogram, and
      a test negative component magnitude based on an absolute magnitude of a greatest negative component of the test electrogram; and
    determine whether a cavitary electrogram indicative of the test electrogram sensing electrical activity from the electrode proximate the distal tip of the lead being free within the cavity of the chamber of the heart and not in fixation with the endocardium is indicated based on the at least two parameters, wherein the cavitary electrogram is indicated based on comparison of the test positive component magnitude and the test negative component magnitude; and
  performing at least one action when the cavitary electrogram is indicated, wherein the at least one action is selected from the group consisting of: generating an electrode dislodgement alert, and/or configuring the implanted medical device to disable therapy.

2. The method of claim 1, wherein the test electrogram is selected from the group consisting of: a near-field electrogram, and a unipolar electrogram.

3. The method of claim 1, wherein the method is performed for only a predetermined amount of time following implant of the implanted medical device.

4. The method of claim 3, wherein the predetermined amount of time is less than about six months.

5. The method of claim 1, wherein the test electrogram is obtained at predetermined time intervals after implant of the implanted medical device.

6. The method of claim 1, wherein the test electrogram is obtained in response to one or more of:
  a sufficient decrease in a rectified amplitude of a sensing electrogram which is measured periodically,
  a sufficient increase a pacing threshold detected by the implanted medical device, which is measured periodically, and
  a sufficient decrease in a pacing impedance detected by the implanted medical device, which is measured periodically.

7. The method of claim 1, wherein obtaining the test electrogram comprises recording an electrogram and storing the electrogram in a memory of the implanted medical device.

8. The method of claim 1, wherein the chamber of the heart is selected from the group consisting of: the right ventricle of the heart, the right atrium of the heart, the left ventricle of the heart, and the left atrium of the heart.

9. The method of claim 1, wherein the cavitary electrogram is indicated when the test negative component magnitude exceeds the test positive component magnitude by a predetermined threshold.

10. The method of claim 1, wherein the cavitary electrogram is indicated when the test positive component magnitude is less than a predetermined value.

11. The method of claim 10, wherein the predetermined value is between about 1 mV and about 3 mV.

12. The method of claim 1, wherein the cavitary electrogram is indicated when the test negative component magnitude is within a predetermined range.

13. The method of claim 12, wherein the predetermined range is between about 1 mV and about 5 mV.

14. The method of claim 1, wherein the cavitary electrogram is indicated when the ratio of the test negative component magnitude to the test positive component magnitude is greater than a predetermined value, the test negative component magnitude is within a prespecified negative component range, and the test positive component magnitude is within a prespecified positive component range.

15. The method of claim 14, wherein the predetermined value is one, the negative component range is between about 1 mV to about 5 mV, and the prespecified positive component range is between about 0 mV and about 3 mV.

16. A method of identifying dislodgement of a lead from fixation with the endocardium of a chamber of the heart of a patient, the lead having an electrode being positioned proximate a distal tip of a lead that is configured for fixation with the endocardium of the chamber of the heart of the patient at implant of an implanted medical device, the electrode being operably coupled proximate a proximal end of the lead to an implanted medical device, the method comprising:
  obtaining a test electrogram for the electrode; obtaining a baseline electrogram at a time before obtaining the test electrogram when the electrode is known to be in fixation with the endocardium;

using a processor to determine:

a baseline positive component magnitude based on an absolute magnitude of a greatest positive component of the baseline electrogram, and a baseline negative component magnitude on an absolute magnitude of a greatest negative component of the baseline electrogram; and whether a cavitary electrogram indicative of the test electrogram sensing electrical activity from the electrode proximate the distal tip of the lead being free within the cavity of the chamber of the heart and not in fixation with the endocardium is indicated based on the at least two parameters, wherein the cavitary electrogram is indicated based on comparison of the test electrogram to at least one of the baseline positive component magnitude and the baseline negative component magnitude; and performing at least one action when the cavitary electrogram is indicated, wherein the at least one action is selected from the group consisting of: generating an electrode dislodgement alert, and/or configuring the implanted medical device to disable therapy.

17. The method of claim 16, wherein the cavitary electrogram is indicated when a ratio of the test negative component magnitude to the baseline negative component magnitude is greater than or equal to three.

18. The method of claim 16, further comprising:
calculating a first ratio of the baseline positive component magnitude to the baseline negative component magnitude; and
calculating a second ratio of the test negative component magnitude to the test positive component magnitude;
wherein the cavitary electrogram is indicated when the first ratio exceeds a first predetermined threshold and the second ratio exceeds a second predetermined threshold.

19. The method of claim 16, further comprising:
calculating a first ratio of the baseline positive component magnitude to the baseline negative component magnitude; and
calculating a second ratio of the test negative component magnitude to the test positive component magnitude;
wherein the cavitary electrogram is indicated when the product of the first ratio and the second ratio exceeds a predetermined threshold.

20. The method of claim 16 wherein the cavitary electrogram is indicated based on at least the relationship between the baseline positive component magnitude and the baseline negative component magnitude.

21. The method of claim 20 wherein if—
the baseline positive component magnitude is greater than 1 mV,
the baseline negative component magnitude is greater than 3 mV, and
the baseline positive component magnitude is less than the baseline negative component magnitude,
then the cavitary electrogram is indicated when—
the test positive component magnitude is less than the value of the baseline positive component magnitude,
the test negative component magnitude is less than 5 mV, and
the test positive component magnitude is less than less than the test negative component magnitude.

22. The method of claim 21 wherein the cavitary electrogram is indicated when the test positive component magnitude is less than 1 mV.

23. The method of claim 16, wherein the test electrogram is selected from the group consisting of: a near-field electrogram, and a unipolar electrogram.

24. The method of claim 16, wherein the method is performed for only a predetermined amount of time following implant of the implanted medical device.

25. The method of claim 24, wherein the predetermined amount of time is less than about six months.

26. The method of claim 16, wherein the test electrogram is obtained at predetermined time intervals after implant of the implanted medical device.

27. The method of claim 16, wherein the test electrogram is obtained in response to one or more of:
a sufficient decrease in a rectified amplitude of a sensing electrogram which is measured periodically,
a sufficient increase a pacing threshold detected by the implanted medical device, which is measured periodically, and
a sufficient decrease in a pacing impedance detected by the implanted medical device, which is measured periodically.

28. The method of claim 16, wherein obtaining the test electrogram comprises recording an electrogram and storing the electrogram in a memory of the implanted medical device.

29. The method of claim 16, wherein the chamber of the heart is selected from the group consisting of: the right ventricle of the heart, the right atrium of the heart, the left ventricle of the heart, and the left atrium of the heart.

* * * * *